(12) United States Patent
Arashida et al.

(10) Patent No.: US 9,045,784 B2
(45) Date of Patent: Jun. 2, 2015

(54) METHOD FOR PRODUCTION OF EUGLENA CONTAINING WAX ESTER AT HIGH CONTENT, AND METHOD FOR PRODUCTION OF WAX ESTER

(75) Inventors: Ryo Arashida, Bunkyo-ku (JP); Sharbanee Mitra, Bunkyo-ku (JP)

(73) Assignee: Euglena Co., Ltd., Tokyo (JP)

( * ) Notice: Subject to any disclaimer, the term of this patent is extended or adjusted under 35 U.S.C. 154(b) by 0 days.

(21) Appl. No.: 13/811,120

(22) PCT Filed: Jul. 13, 2011

(86) PCT No.: PCT/JP2011/066015
§ 371 (c)(1),
(2), (4) Date: Jan. 18, 2013

(87) PCT Pub. No.: WO2012/011421
PCT Pub. Date: Jan. 26, 2012

(65) Prior Publication Data
US 2013/0115666 A1    May 9, 2013

(30) Foreign Application Priority Data
Jul. 20, 2010   (JP) ................................. 2010-163370

(51) Int. Cl.
  *C12P 7/64*    (2006.01)
  *C12N 1/12*    (2006.01)
  *C12N 15/82*   (2006.01)

(52) U.S. Cl.
  CPC ... *C12P 7/64* (2013.01); *C12N 1/12* (2013.01); *C12N 15/8247* (2013.01); *C12P 7/6463* (2013.01)

(58) Field of Classification Search
  CPC ........... C12P 7/64; C12P 7/6463; C12N 1/12; C12N 15/8247
  See application file for complete search history.

(56) References Cited

FOREIGN PATENT DOCUMENTS

| JP | 1984118090 | 7/1984 |
|----|------------|--------|
| JP | 61254193   | 11/1986 |
| JP | 1991065948 | 10/1991 |
| JP | 1993027384 | 4/1993 |

(Continued)

OTHER PUBLICATIONS

Singh et al., Lipid and hydrocarbon production by *Botryococcus* spp. under nitrogen limitation and anaerobiosis, World Journal of Microbiology and Biotechnology, 8, 121-124, 1992.*

(Continued)

*Primary Examiner* — Karen Cochrane Carlson
*Assistant Examiner* — Jennifer M. H. Tichy
(74) *Attorney, Agent, or Firm* — Sughrue Mion, PLLC

(57) ABSTRACT

Provided is a method for producing a *euglena* highly containing a wax ester, comprising aerobically culturing a microalga *euglena* by photosynthesis using carbon dioxide as a carbon source, then further culturing the microalga *euglena* under nitrogen-starvation conditions to increase paramylon accumulation per cell, and subsequently putting the microalga *euglena* under anaerobic conditions, so that a *euglena* highly containing a wax ester can be produced; and a method for producing a wax ester.
The present invention relates to a method for producing a *euglena* highly containing a wax ester. The method comprises a first step of aerobically culturing a microalga *euglena*, a second step of further culturing a medium under nitrogen-starvation conditions, and a third step of retaining the cells under anaerobic conditions.

13 Claims, 3 Drawing Sheets

(56) References Cited

FOREIGN PATENT DOCUMENTS

| JP | 1994113819 | 4/1994 |
|---|---|---|
| JP | 07203849 | 8/1995 |

OTHER PUBLICATIONS

Zeiler et al., The use of microalgae for assimilation and utilization of carbon dioxide from fossil fuel-fired power plant flue gas, Energy Conyers. Mgmt., vol. 36, No. 6-9, pp. 707-712, 1995.*

Deng et al., Microalgae: A promising feedstock for biodiesel, African Journal of Microbiology Research vol. 3(13) pp. 1008-1014 Dec. 2009.*

Sumida et al., "Ammonia- and Light-Induced Degradation of Paramylum in *Euglena gracilis*", Plant Cell Physiol., 28(8):1587-1592 (1987).

International Search Report for PCT/JP2011/066015 dated Sep. 13, 2011.

International Preliminary Report on Patentablity for PCT/JP2011/066015 dated Feb. 12, 2013.

Garcia-Ferris et al., "Correlated Biochemical and Ultrastructural Changes in Nitrogen-starved *Euglena gracilis*", J. Phycol., 32:953-963 (1996).

Tani et al., "Liquid Wax Ester Production by *Euglena gracilis*", Agric. Biol. Chem., 51(1):225-230 (1987).

Coleman et al., "Environmental Control of Carbohydrate and Lipid Synthesis in *Euglena*", Plant Cell Physiol., 29(3):423-432 (1988).

Miyashita, "For development of microalgae energy industry in Japan, What should Japan do for the new revolutionary industry where Japan is behind?", J-Phoenix Research Inc., http://www.j-phoenix.com/pages/48/file20100228.pdf, published Dec. 10, 2009.

Miyazawa et al., "Experimental Method for Biochemistry 9 Introduction for Lipid and Oxidized Lipid Analysis", Gakkai Shuppan Center, pp. 44-49 and 72-77, published Sep. 15, 1978.

Fixter et al., "Structure, Distribution and Function of Wax Esters in *Acinetobacter calcoaceticus*", Journal of General Microbiology, 132:3147-3157 (1986).

Japan Oil Chemist's Society, "The Basic and Applied Science of Fats, Oils, and other Lipids", pp. 66-67, 240-241 and 280-281 (2005).

Regnault et al., "Lipid Composition of *Euglena gracilis* in relation to carbon-nitrogen balance", Phytochemistry, 40(3):725-733 (1995); [only pp. 725-727 provided herewith].

Chinese Office Action for Application No. 201180035039.1 dated Sep. 27, 2013.

Office Action for Korean Application No. 10-2013-7002121 dated Jun. 13, 2013.

* cited by examiner

METHOD FOR PRODUCTION OF EUGLENA CONTAINING WAX ESTER AT HIGH CONTENT, AND METHOD FOR PRODUCTION OF WAX ESTER

This application is a 371 National Stage Entry of PCT/JP2011/066015 filed Jul. 13, 2011, which claims priority from Japanese Patent Application No. 2010-163370, filed on Jul. 20, 2010, the contents of which are incorporated herein by reference in their entirety.

TECHNICAL FIELD

The present invention relates to a method for producing a *euglena* highly containing a wax ester that enables production of a microalga *euglena* highly containing a wax ester to be a source of biofuel at low energy and low cost.

BACKGROUND ART

These days, the problem of global warming has attracted considerable attention, and controlling emissions of carbon dioxide gas, which is one of greenhouse gases, and reducing carbon dioxide concentration in the atmosphere by fixing carbon dioxide are big challenges.

Under these circumstances, using fossil fuels containing fixed carbon dioxide as energy leads to a release of the fixed carbon dioxide into the atmosphere once again, which causes an environmental problem. In addition, since fossil fuels are a finite resource, there is a problem of depletion.

In order to solve the above problems, a fuel source other than fossil fuels is required, and expectations for development of biofuels derived from higher plants and algae have increased.

As a higher plant that is a candidate for a biofuel source, soybean, corn, palm and the like have been known. Using an edible crop as a source causes a problem with concern over food shortages. Meanwhile, while production from inedible plants such as Jatropha and Camelina has also been developed, it has a problem that the production volume per unit area is small.

Meanwhile, photosynthetic microorganisms and protozoan widely living in ponds and marsh have photosynthetic capacity as same as plants, and carbohydrate and lipid are biosynthesized from water and carbon dioxide, and accumulated in cells in several tens % by mass. It has been known that the production volume is larger than that derived from a plant, and is 10 times larger or more of that derived from a palm that is considered to have high production volume of carbohydrate and lipid, per unit area.

Incidentally, a microalga *euglena* that is one of the photosynthetic microorganisms is one group of flagellates, and includes *euglena* that is famous as motile algae. Most *euglena* have chloroplasts and produce energy through photosynthesis, and some *euglena* feed by phagocytosis or absorb nutrients. *Euglena* is a genus classified into both zoology and botany.

In zoology, the order Euglenida is in the order belonging to the subclass Phytomastigophorea, of the class Mastigophora in the division Protozoa, and is composed of three suborders, Euglenoidina, Peranemoidina, and Petalomonadoidina.

In Euglenoidina, as genera, *Euglena, Trachelemonas, Strombonas, Phacus, Lepocinlis, Astasia*, and *Colacium* are included. In botany, the order Euglenales is, of the class Euglenophyceae coextensive with the division Euglenophyta, and the genera in this order are, including *euglena*, the same as in animal classification table.

*Euglena* accumulates paramylon in the cells as carbohydrate. Paramylon is macromolecule particles obtained by polymerizing about 700 glucoses by beta-1,3-bonds.

When *euglena* is put under anaerobic conditions, wax ester fermentation in which paramylon, as a storage polysaccharide, is decomposed to finally produce a wax ester of a fatty acid, and a fatty alcohol is performed.

Non-Patent Document 1 describes that, after culturing *euglena* under light irradiation, while paramylon accumulation per cell is increased in an experimental area replaced by a nitrogen source-free medium, the content of paramylon per cell is reduced in an experimental area replaced by a nitrogen source-added medium.

Patent Document 1 describes that *euglena* is aerobically cultured and then put under anaerobic conditions, so as to ferment storage polysaccharide paramylon into a raw ester (wax ester).

Patent Document 2 describes a method for producing an unsaturated wax ester that is an alternative source of sperm oil used as a quality lubricant, by aerobically culturing a microalga *euglena* and adding an unsaturated fatty acid thereto, and then putting the culturing under anaerobic conditions, so as to ferment storage polysaccharide paramylon to transform into a wax ester.

CITATION LIST

Patent Document

Patent Document 1: JP-A-H03-65948
Patent Document 2: JP-A-H05-27384

Non-Patent Document

Non-Patent Document 1: Sumida et al., Ammonia- and Linght-Induced Degradation of Paramylum in *Euglena gracilis*. Plant Cell Physiol. 28(8). P1587 to 1592 (1987)

DISCLOSURE OF THE INVENTION

Technical Problem

However, Non-Patent Document 1 only describes about control of paramylon decomposition and does not suggest a combination with wax ester fermentation.

In addition, Patent Document 1 only discloses general methods such as adding an organic substance such as glucose as a carbon source, and culturing under normal photosynthetic conditions, as an aerobic culturing method.

In the manufacture of biofuel, a culturing method using a carbon source such as glucose is not worth the cost, and also does not lead to the fixation of carbon dioxide.

Moreover, although the object of the technique disclosed in Patent Document 2 is to obtain an unsaturated wax ester at a high yield, a saturated wax ester is more desirable as a source of biofuel.

An object of the present invention is to solve each problem described above, and to provide a method for producing a *euglena* highly containing a wax ester, comprising aerobically culturing a microalga *euglena* by photosynthesis using carbon dioxide as a carbon source, then further culturing the microalga *euglena* under nitrogen-starvation conditions to increase paramylon accumulation per cell, and subsequently putting the microalga *euglena* under anaerobic conditions, so that a *euglena* highly containing a wax ester is produced; and a method for producing a wax ester.

Solution to Problem

The above problems can be solved by a method for producing a *euglena* highly containing a wax ester according to the present invention, comprising a first step of aerobically culturing a microalga *euglena*, a second step of putting under nitrogen-starvation conditions a medium in which the microalga *euglena* is cultured and further culturing the medium, and a third step of retaining the cells under anaerobic conditions.

As described above, the series of the steps of aerobic culturing, further culturing under nitrogen-starvation conditions, and retainment of the cells under anaerobic conditions is carried out, so that a *euglena* with a high content of a wax ester can be efficiently produced.

Specifically, through the culturing under nitrogen-starvation conditions in Step 2, carbohydrate can be sufficiently accumulated in *euglena*.

Therefore, the cells cultured in Step 2 are put under anaerobic conditions, so that the carbohydrate sufficiently accumulated in Step 2 is transformed into a wax ester in Step 3; and accordingly, wax ester accumulation in Step 3 is dramatically increased.

In other words, when Step 1, Step 2, and Step 3 described above are combined, an advantageous effect that wax ester accumulation is dramatically increased is exhibited.

In addition, the cells of *euglena* cultured under nitrogen-starvation conditions exhibit a green color same as those during culturing even immediately after anaerobic treatment, in a state where almost no cell is killed, and the cell size does not change compared to that before anaerobic treatment.

Specifically, when anaerobic treatment is carried out in a nitrogen source-free medium, an advantageous effect that the survival rate of cells of *euglena* is significantly improved compared to that in a nitrogen source-contained medium is also exhibited.

In addition, at that time, it is preferable for the nitrogen-starvation conditions to be created by replacing the medium with a nitrogen source-deficient medium, since the nitrogen-starvation conditions can be efficiently created.

As described above, the series of steps of aerobic culturing, further culturing under nitrogen-starvation conditions, and retainment of the cells under anaerobic conditions is carried out, so that a *euglena* with a high content of a wax ester can be efficiently produced.

Specifically, it is preferable, in the first step, for the aerobic culturing of the microalga *euglena* to be started in a nitrogen source-free medium, also the culturing is continuously and aerobically carried out with appropriate adjustment of the feeding amount and addition of a nitrogen source, and feeding of nitrogen source is stopped at the point where the cell concentration reaches a certain level, and in the second step, for the medium to be put under nitrogen-starvation conditions to perform further culturing.

Furthermore, specifically, in the first step, it is preferable for a carbon dioxide gas to be allowed to flow, so that a carbon dioxide source and an oxygen source mixed thereto are provided, and it is more preferable for the carbon dioxide gas to be those emitted from power plants.

The configuration as described above enables to increase culturing amount for industrialization, and mass production can be performed.

Furthermore, since a carbon dioxide gas obtainable as an exhaust gas can be effectively utilized, it has a cost advantage and is also a quite useful technique for the environment.

Here, the feeding of nitrogen source is stopped in Step 1, thus *euglena* assimilates all nitrogen source, and the nitrogen-starvation condition in Step 2 is consequently created.

In addition, in the third step, it is preferable for anaerobic treatment to be carried out by at least one method selected from inert gas ventilation, standing treatment, and concentration by centrifugation.

One method may be selected or a plurality of methods may be combined.

Moreover, according to a method for producing a wax ester according to the present invention, the above problems are solved by carrying out, using the *euglena* highly containing a wax ester produced by the method for producing a *euglena* highly containing a wax ester as described above, a step of extracting an oily fraction with an organic solvent to obtain an extract, and concentrating the extract to obtain a wax component, and a step of separating a wax ester from the wax component with a column to perform a first purification.

As described above, in the present invention, a wax ester component can be easily purified from the cultured *euglena*.

A large amount of this *euglena* can be easily cultured in a state highly containing a wax ester, according to the methods described above.

Thus, according to the present invention, it is possible to stably provide a quality clean fuel using *euglena* cultured in a large amount.

Specifically, it is preferable for the concentration to be preferably carried out within a range of $50° C. \pm 10° C$.

When the temperature is lower than this, there is a possibility of bumping due to the viscosity of the wax component, and blowout of the wax component into an evaporator as a concentrator.

More specifically, it is preferable for a step of hydrolyzing the wax ester obtained by the step of performing a first purification to perform a second purification to be carried out as a next step.

Due to this configuration as described above, the culturing crudely produced in the first purification can be further purified in the second purification, and thus fuel with an enhanced quality can be provided.

Specifically, after the step of performing a first purification, hydrolysis is carried out in the second purification, so that the carbon chain is shortened, volatility is increased, and value as a fuel is enhanced.

In addition, it is preferable for, in the step of performing a first purification, hexane or a mixed solvent of hexane and ether to which ether to be mixed in an amount of 10% by volume or less is used as an eluting solvent applied to the column.

This configuration as described above is preferable since chlorophyll can be efficiently separated and also other pigments can be effectively eliminated.

Accordingly, fuel with an enhanced quality can be provided.

The wax ester produced from *euglena* through the method for producing a wax ester is a quality biofuel, and these can be stably provided in a large amount.

In addition, this biofuel is a clean energy and greatly contributes to improvement in environmental problems and the like.

As described above, in order to solve the above problems, a method for producing a wax ester according to the present invention includes: a culturing step of aerobically culturing *euglena*, after the culturing step, a culturing step of further culturing under nitrogen-starvation conditions so as to accumulate carbohydrate, and an anaerobic fermentation step of putting the cultured cells under anaerobic conditions so as to transform carbohydrate into a wax ester.

Advantageous Effects of the Invention

According to the present invention, a biomass feedstock containing much fats and oils can be inexpensively provided from a carbon dioxide fixed by photosynthesis.

Also, the manufacture of biofuel according to the present invention also leads to the improvement in the energy self-sufficiency rate.

DETAILED DESCRIPTION OF THE INVENTION

Hereinbelow, an embodiment of the present invention will be described based on the drawings.

Here, the configuration described below is not intended to limit the present invention, and various modifications can be made within the scope of the present invention.

This embodiment relates to a method for producing a *euglena* highly containing a wax ester by culturing *euglena* under aerobic conditions, followed by further culturing under nitrogen-starvation conditions, then putting the medium under anaerobic conditions.

First Embodiment

Figure 1:
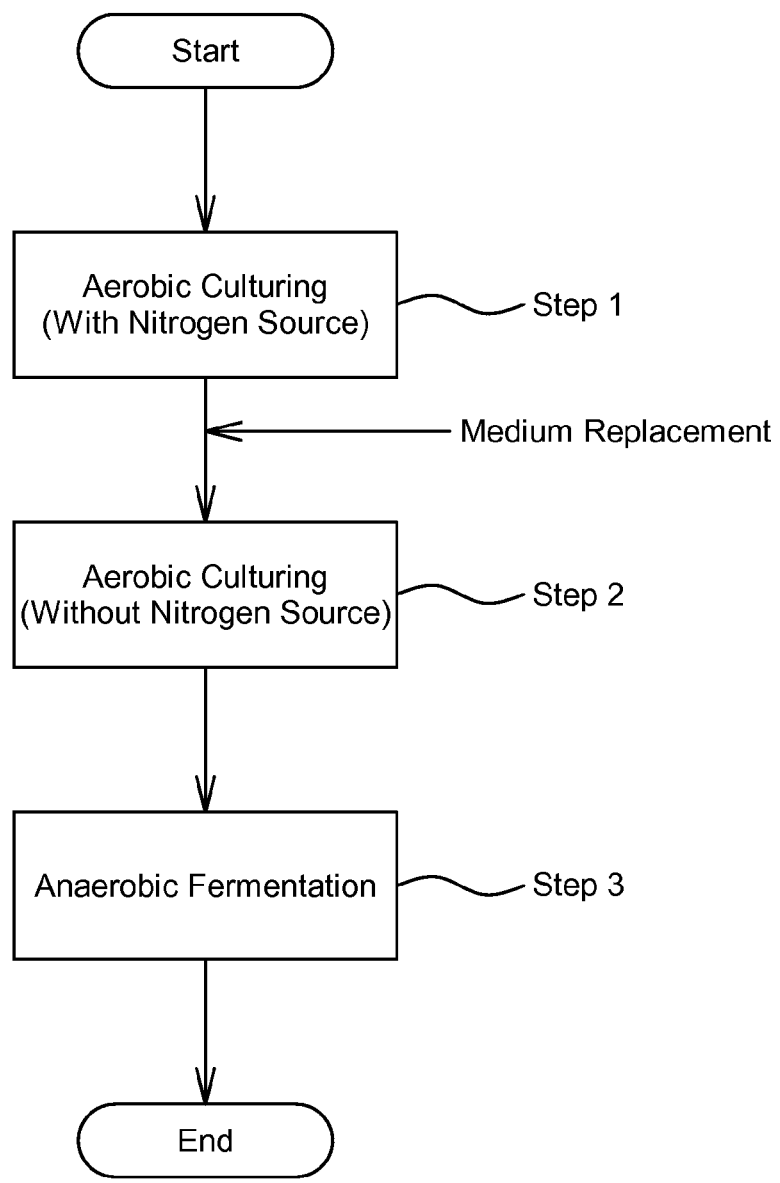
FIG. 1 is a flow chart showing a method for producing a *euglena* highly containing a wax ester according to a first embodiment of the present invention.

According to FIG. 1, a first embodiment of the method for producing a *euglena* highly containing a wax ester according to the present invention will be described.

The present production method includes Step 1 of aerobically culturing *euglena* in a nitrogen source-added medium (corresponding to a first step), Step 2 of replacing the medium with a nitrogen source-free medium and aerobically culturing the *euglena* (corresponding to a second step), and Step 3 of performing anaerobic treatment and fermenting carbohydrate into a wax ester (corresponding to a third step).

First, although the culturing of *euglena* in Step 1 can be carried out by allowing air to flow through the medium as a carbon dioxide source, it is more preferable for a carbon dioxide gas to be allowed to flow through the medium to increase the culturing efficiency.

Specifically, by taking advantage of air and a carbon dioxide gas also containing oxygen, an aerobic culturing is carried out.

A carbon dioxide gas can be allowed to flow, for example, by utilizing a combustion exhaust gas emitted from plants, power plants, and the like. At this time, it is preferable to remove dust, NOx and SOx in a combustion exhaust gas by a dust collector, denitrator, desulfurizer, and the like. In addition, for stirring, common techniques can be used such as airlift system by ventilation, a method using a stirring blade, and the like.

Although light irradiation can also be performed by irradiating an artificial light such as fluorescent light, it is desirable to culturing only with sunlight for culturing with low energy and low cost.

In addition, it is preferable for the water temperature of the medium to be controlled to 29±1° C.

However, it is preferable to avoid temperature control so as not to input an energy for water temperature control, or even if the water temperature control is performed, minimum controls are preferable such as cooling so as to avoid high temperature at which *euglena* is killed and warming so as to avoid excessive water temperature decrease during the winter months and nighttime.

As a composition of the medium for *euglena*, for example, a modified Cramer-Myers medium (1.0 g/L $(NH_4)_2HPO_4$, 1.0 g/L $KH_2PO_4$, 0.2 g/L $MgSO_4.7H_2O$, 0.02 g/L $CaCl_2.2H_2O$, 0.05 g/L EDTA.2Na, 3 mg/L $Fe_2(SO_2)_3.7H_2O$, 1.8 mg/L $MnCl_2.4H_2O$, 1.5 mg/L $CoSO_4.7H_2O$, 0.4 mg/L $ZnSO_4.7H_2O$, 0.2 mg/L $Na_2MoO_4.2H_2O$, 0.02 g/L $CuSO_4.5H_2O$, 0.1 mg/L thiamine hydrochloride (vitamin $B_1$), cyanocobalamin (vitamin $B_{12}$), (pH 3.5)) can be used. It is also possible to transform $(NH_4)_2HPO_4$ into $(NH_4)_2SO_4$ and $NH_3$ aq.

Of course, a composition of the medium is not limited to these compositions.

Although pH of the medium may be within a range of 2 to 7.5, it is preferable to be adjusted to 3.5 or 5.5. Particularly, when the medium is acidified to a pH of 4.5 or less, contamination of zooplankton, cells, and the like can be effectively controlled.

Subsequently, in Step 2, the medium is replaced by a nitrogen source-free medium, and further culturing is carried out.

For a composition of the nitrogen source-free medium in Step 2, for example, a Resting medium, 1% mannitol, 0.2% $MgCl_2. 6H_2O$ and 0.14% $KH_2PO_4$ can be used.

Of course, a composition of the medium is not limited to these as long as the medium does not contain a nitrogen source.

Subsequently, in Step 3, anaerobic treatment of the cultured *euglena* is carried out.

Anaerobic treatment is normally carried out by allowing an inert gas such as nitrogen gas to flow through the medium after culturing. In addition, anaerobic treatment can also be carried out by allowing the medium to still-stand. When the medium is allowed to still-stand without stirring, the cells are settled down and the density is increased, so that a shortage of oxygen is induced. Anaerobic treatment may be also carried out by making a high density state by centrifugation.

The pH at this time is acceptable as long as it is not an extremely low or high value, and the presence or absence of light irradiation has no effect on wax ester fermentation. The acceptable retention temperature is not so high that *euglena* is killed and is not so low that the medium freezes. Normally, wax ester fermentation ends in 6 hours to 72 hours.

Through the culturing under nitrogen-starvation conditions in Step 2, carbohydrate can be sufficiently accumulated in *euglena*.

Therefore, since the cells which have been cultured in Step 2 are put under anaerobic conditions, the carbohydrate which has sufficiently been accumulated in Step 2 is transformed into a wax ester in Step 3, and accordingly, wax ester accumulation in Step 3 is dramatically increased.

In other words, Step 1, Step 2, and Step 3 described above exhibits, when they are combined together, an advantageous effect that wax ester accumulation is dramatically increased, which cannot be obtained by each single step.

In addition, as detailed in the following examples, the cells of *euglena* cultured under nitrogen-starvation conditions exhibit a green color even immediately after anaerobic treatment same as that during culturing, almost no cell is killed, and the cell size does not change compared to that before anaerobic treatment.

Specifically, when anaerobic treatment is carried out in a nitrogen source-free medium, an advantageous effect that the survival rate of cells of *euglena* is significantly improved compared to that obtained by a nitrogen source-contained medium is also exhibited.

As described above, the combination of Step 1, Step 2, and Step 3 described above achieves a *euglena* with a high cell activity containing a significantly large amount of wax ester compared to the background art.

Second Embodiment

Figure 2:
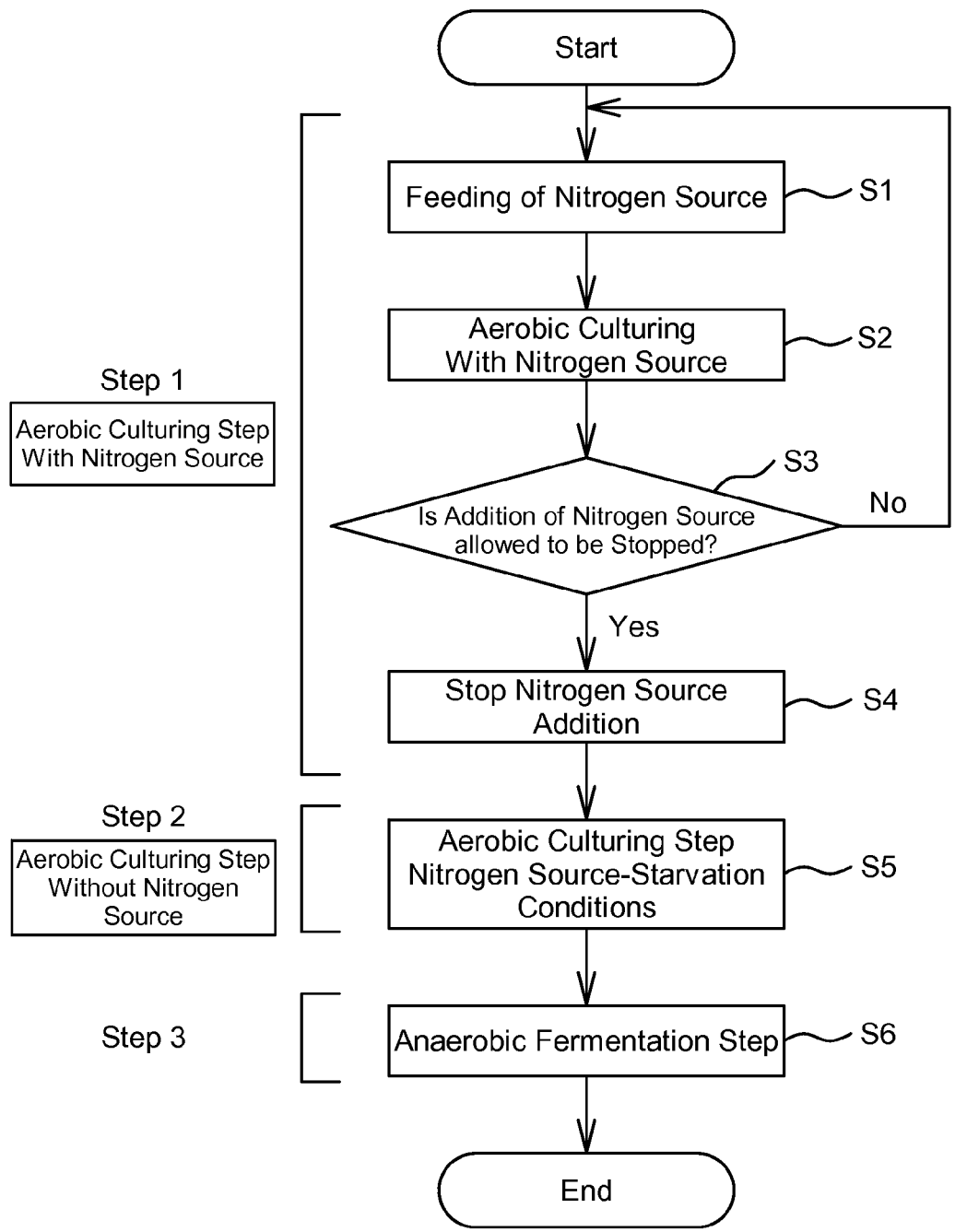
FIG. 2 is a flow chart showing a method for producing a *euglena* highly containing a wax ester according to a second embodiment of the present invention.

According to FIG. 2, a second embodiment of the method for producing a *euglena* highly containing a wax ester according to the present invention will be described.

Since the composition of the medium, the culturing conditions and the like are the same as the first example, the same description is omitted, and only the difference will be described.

The aerobic culturing step in Step 1 uses a medium in which a nitrogen source is removed from the modified Cramer-Myers medium in Step 1 of the first embodiment.

Specifically, in an early stage, an aerobic culturing of *euglena* is started in a nitrogen source-free medium.

In Step 1, first, in Step S1, a nitrogen source is fed to the medium to which *euglena* is inoculated.

Then, an aerobic culturing is carried out by Step S2.

Subsequently, whether or not the addition of nitrogen source is allowed to be stopped is determined in Step S3.

In Step 3, when it is determined that the addition of nitrogen source is not to be stopped (Step S3: No), the treatment returns to Step S1, and a nitrogen source is fed.

In addition, in Step 3, when it is determined that the addition of nitrogen source is to be stopped (Step S3: Yes), the treatment moves on to Step S4, and the addition of nitrogen source is stopped.

Specifically, in Step 1, a nitrogen source is gradually fed, and an aerobic culturing containing a nitrogen source is carried out.

The feed amount and the like of this nitrogen source depend on the conditions of weather, temperature and the like, and are properly adjusted in consideration of these conditions.

Here, as a rough standard of stopping the addition of nitrogen source, in this embodiment, in consideration of the above conditions and the like, for example, the point where the cell concentration reaches a certain level and the like are selected.

Subsequently, in Step 2 (Step S5), an aerobic culturing is continuously carried out for a required period.

Although, at this time, the nitrogen source remains at an early stage, the nitrogen source is assimilated by *euglena* over time, and the medium is put under nitrogen source-starvation conditions.

Therefore, so-called culturing step "Aerobic Culturing Step Without Nitrogen Source" of Step 2 is established.

Subsequently, in Step S6, an anaerobic fermentation step of Step 3 is carried out, and this step is the same as in the first embodiment.

As a method of adding a nitrogen source, a method of inputting a nitrogen source at the start of culturing at a time is also considered.

In this case, the nitrogen source remains at an early stage, the nitrogen source is assimilated by *euglena* over time, and the medium is put under nitrogen source-starvation conditions.

Therefore, an aerobic culturing under nitrogen-starvation conditions, so-called, culturing step "Aerobic Culturing Step Without Nitrogen Source" is established.

The method for producing a *euglena* highly containing a wax ester according to the second embodiment is effective in a large scale industrial manufacturing line.

Specifically, it is possible to carry out culturing in continuous operation, so as to eliminate centrifugation operation for medium replacement or the like.

Accordingly, the energy use required for culturing is reduced, and the production method is effectively applied to the mass production of a *euglena* highly containing a wax ester.

Figure 3:
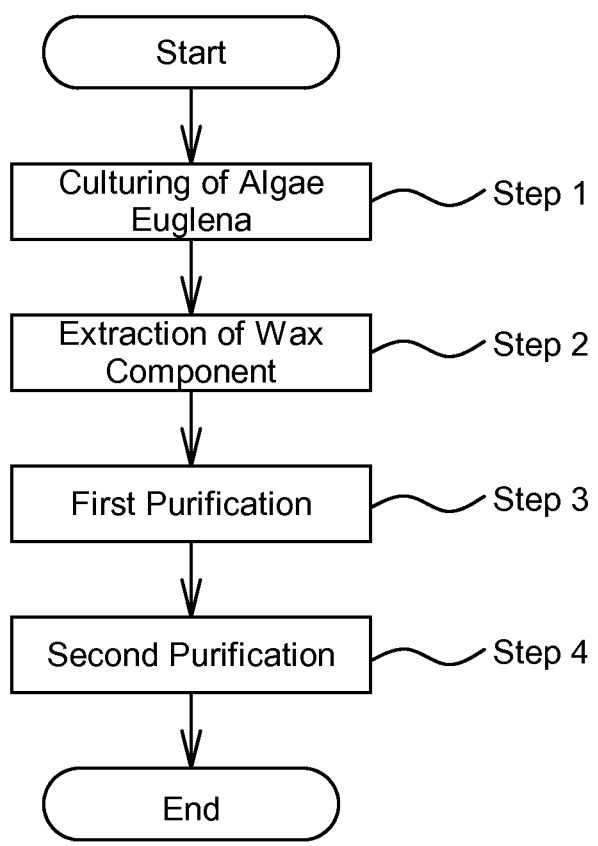
FIG. 3 is a flow chart showing a method for producing a wax ester according to an embodiment of the present invention.

Subsequently, in reference to FIG. 3, the step of the method for producing a wax ester from *euglena* according to this embodiment will be described.

First, *euglena* is cultured in Step 1. This is the culturing according to the production step according to the first embodiment or second embodiment.

Subsequently, a wax ester is extracted in Step 2. Therefore, the component obtained in Step 2 is subjected to a first purification in Step 3, and then subjected to a second purification in Step 4, to obtain a wax ester.

In the first purification, a wax ester is extracted from *euglena* with an organic solvent, and in the second purification, separation and purification of wax ester with a column is carried out.

The wax ester purified as described above can be effectively utilized as a biofuel containing this wax ester.

Examples (Regarding Method for Producing a *Euglena* Highly Containing a Wax Ester)

Hereinbelow, the *euglena* highly containing a wax ester according to the present invention will be specifically described showing an example.

In this example, *Euglena gracilis* Z strain was used.

The medium was prepared by sterilizing in an autoclave a modified Cramer-Myers medium (1.0 g/L $(NH_4)_2HPO_4$, 1.0 g/L $KH_2PO_4$, 0.2 g/L $MgSO_4.7H_2O$, 0.02 g/L $CaCl_2.2H_2O$, 0.05 g/L EDTA.2Na, 3 mg/L $Fe_2(SO_2)_3.7H_2O$, 1.8 mg/L $MnCl_2.4H_2O$, 1.5 mg/L $CoSO_4.7H_2O$, 0.4 mg/L $ZnSO_4.7H_2O$, 0.2 mg/L $Na_2MoO_4.2H_2O$, 0.02 g/L $CuSO_4.5H_2O$, 0.1 mg/L thiamine hydrochloride (vitamin $B_1$), cyanocobalamin (vitamin $B_{12}$), (pH 5.5)).

(Step 1: Aerobic culturing)

A 1 L-volume shake flask was charged with 880 ml prepared medium, thereafter, an alga body of *euglena* was inoculated so as to have an initial concentration of about 0.05 g/L, and was subjected to shaking culturing in a growth chamber (manufactured by SANYO Electric Co., Ltd, GROWTH CABINET) set at 29° C. for 9 days. The light irradiation intensity was set to about 100 μmol/($m^2$·s), and the light irradiation period was set to 24 consecutive hours. A carbon dioxide gas with a ventilation density of 10% was supplied in the flask.

(Step 2: Nitrogen-deficient culturing)

After culturing for 9 days, the culturing fluid was divided into two, and each was replaced with a nitrogen source-free medium and a nitrogen source-contained medium.

Specifically, 420 ml each of a culturing fluid was taken from 880 ml of the culturing fluid, each centrifuged, and then the supernatant was discarded. Thereafter, 420 ml of the modified Cramer-Myers medium (hereinafter, nitrogen source-deficient medium) 1.0 g/L $KH_2PO_4$, 0.2 g/L $MgSO_4.7H_2O$, 0.02 g/L $CaCl_2.2H_2O$, 0.05 g/L $EDTA.2Na$, 3 mg/L $Fe_2(SO_2)_3.7H_2O$, 1.8 mg/L $MnCl_2.4H_2O$, 1.5 mg/L $CoSO_4.7H_2O$, 0.4 mg/L $ZnSO_4.7H_2O$, 0.2 mg/L $Na_2MoO_4.2H_2O$, 0.02 g/L $CuSO_4.5H_2O$, 0.1 mg/L thiamine hydrochloride (vitamin $B_1$), cyanocobalamin (vitamin $B_{12}$), (pH 5.5) from which a nitrogen source was removed was added to one precipitation, 420 ml of a new CM medium (containing a nitrogen source) was added to other precipitation, and each was suspended.

The culturing fluid replaced with a nitrogen source-deficient medium is referred to as Sample 1, and the culturing fluid replaced with a new CM medium is referred to as Sample 2, hereinafter.

After replacing the medium, Sample 1 and Sample 2 were both further subjected to shaking culturing in a growth chamber set at 29° C. for 48 hours. The light irradiation intensity was set to about 100 μmol/(m²·s), and the light irradiation period was set to 24 consecutive hours. A carbon dioxide gas with a ventilation density of 10% was supplied to the flask.

(Step 3: Anaerobic treatment)

After replacing the medium and culturing the medium, dry weights of Sample 1 and Sample 2 were measured (Table 1A), the flask was sealed tightly and shielded in a growth chamber set at 29° C. and allowed to still-stand, so as to put the cells under anaerobic conditions.

The method of measuring a dry weight of *euglena* cells in the culturing fluid is as described below.

The cells were dried in a dryer at 105° C. for 30 minutes in advance, and 1 ml of the culturing fluid was filtered with a glass filter GS-25 (manufactured by ADVANTEC MFS, INC.) with a pore size of about 1 μm of which weight had been measured. Next, the glass filter was located in a dryer set at 105° C. and dried for 1 hour. Thereafter, the dried glass filter was dehumidified for 20 minutes and cooled while pressure is decreased in a vacuum desiccator, then the weight was measured with a precision balance. The weight difference of the filter before and after filtration was referred to as a dry weight per 1 ml.

After carrying out anaerobic treatment for 48 hours, both samples were collected. Using a centrifuge (manufactured by KOKUSAN Co. Ltd., H-103FN), 400 ml of the collected culturing fluid was centrifuged at 3000 rpm at ordinary temperature for minutes, then the supernatant was discarded, and the precipitated alga body was collected. The collected alga body was frozen and then lyophilized.

(Extraction of lipid)

A 50 ml-volume eggplant-shaped flask was dried in a vacuum desiccator for 1 hour or so, and the weight of the eggplant-shaped flask itself was measured. The lyophilized *euglena* powder was crushed with a spatula or the like, and the powder was weighed into a 50 ml-volume Erlenmeyer flask. At this time, the weight of Sample 1 was 0.693 g, and the weight of Sample 2 was 0.480 g (Table 1B).

Next, 20 ml of hexane was added to each sample and suspended. In order to further crush clumps of the powder, the suspension was crushed with ultrasonic wave for 30 seconds. The supernatant after spontaneous precipitation was transferred to a 50 ml-volume glass centrifuge tube with a lid with a Pasteur pipette and centrifuged at 3000 rpm for 10 minutes, and the supernatant was filtered through a filter paper (ADVANTEC MFS, INC., NO. 2).

The extraction operation was repeated for a total of 9 times while replacing the solvent.

Specifically, the above extraction operation was repeated 3 times using hexane, then the same extraction operation was carried out 3 times with replacing the organic solvent with acetone, and finally extraction operation was carried out 3 times using a solvent obtained by mixing hexane and acetone at a rate of 1:1.

Therefore, the eggplant-shaped flask with filtrate inside was warmed in a hot water bath at 40 to 50° C. using a rotary evaporator (manufactured by TOKYO RIKAKIKAI CO, LTD, ROTARY VACCUUM EVAPORATOR) to evaporate hexane and acetone. Inside of the eggplant-shaped flask was washed using a small amount of hexane and transferred to the weighed eggplant-shaped flask. This operation was repeated 4 times, and then hexane was evaporated in the same manner as above.

The eggplant-shaped flask was covered with aluminum foil, put in a vacuum desiccator, and dried for 30 minutes to 1 hour or so while evaporating remaining hexane.

The weight of the eggplant-shaped flask after extracting a lipid from the *euglena* powder was measured, and the weight of the eggplant-shaped flask itself initially measured was subtracted therefrom, to calculate the weight of the lipid (Table 1C).

Here, most of the lipid extracted through the present extraction method was formed by a wax ester.

As a result of this experiment, the extracted amount of the final crude lipid was 0.188 g from Sample 1 cultured in the nitrogen source-deficient medium and 0.157 g from Sample 2 cultured in the CM nitrogen source-contained medium. Thus, the yield of the crude lipid when cultured in the nitrogen source-deficient medium was larger by 0.031 g (Table 1C).

In addition, the content rate of the crude lipid based on the dry weight before anaerobic treatment was 23% in Sample 1 cultured in the nitrogen source-deficient medium and 16% in Sample 2 cultured in the CM nitrogen source-contained medium. Thus, the content rate of the lipid cultured in the nitrogen source-deficient medium was also larger by 7% (Table 1C/A).

Furthermore, comparing before and after anaerobic treatment, the cell weight was reduced by about 0.120 g in Sample 1, and the cell weight was reduced by 0.507 g in Sample 2 (Table 1B). The color of the culturing fluid of Sample 2 immediately after anaerobic treatment is changed into brown. When observed with a microscope, many cells were killed, and even living cells also became reduced in size. Meanwhile, Sample 1 exhibited a green color even immediately after anaerobic treatment same as that during culturing. When observed with a microscope, almost no cell was killed, and the cell size is not changed compared to that before anaerobic treatment. Based on the above results, it is found that when anaerobic treatment is carried out in a nitrogen source-free medium, the survival rate of cells is significantly improved compared to that in a nitrogen source-contained medium.

The result is summarized in Table 1.

TABLE 1

|  | A<br>Dry weight<br>before anaerobic<br>treatment<br>(g/400 ml) | B<br>Dry weight<br>after anaerobic<br>treatment<br>(g/400 ml) | C<br>Extracted<br>amount of<br>crude lipid<br>(g/400 ml) | C/A<br>Content<br>rate of<br>lipid<br>(%) |
|---|---|---|---|---|
| Sample 1<br>(Nitrogen-<br>deficient<br>medium) | 0.813 | 0.693 | 0.188 | 23 |
| Sample 2<br>(CM medium) | 0.987 | 0.480 | 0.157 | 16 |

Based on the above, in an experimental area put under nitrogen-starvation conditions, the final yield of the lipid is increased, and also the survival rate of cells before and after anaerobic treatment is significantly improved compared to an experimental area cultured in a nitrogen source-contained medium.

(Regarding separation and purification of wax ester)

Subsequently, an embodiment of the procedure for extracting a wax ester from *euglena* and purifying will be described.

In this embodiment, a wax ester stored in *euglena* was extracted and purified using powdered *euglena* (Step 2).

(Ingredients)

| | |
|---|---|
| *Euglena* powder | 10 kg |
| Hexane | 60 L |
| Ether | 1 L |
| Wakogel C-300 | 300 g |

1. Extraction and Filtration (1) 1 kg of *euglena* was weighed and suspended in 2.5 L of hexane (2) The suspension was vigorously stirred with a blender 30 seconds×3 times (3) The mixture was allowed to still-stand at room temperature for 10 minutes to allow *euglena* powder to be settled down spontaneously (4) The supernatant was subjected to suction filtration with a filter paper (5) The sediment was transferred to a Buchner funnel, and the oil component adhered to the sediment was pressed (6) The filtrate in (4) and the collected fluid in (5) were transferred to a eggplant-shaped flask, and concentrated with a rotary evaporator (concentration conditions: temperature of 50° C.±10° C., decompression rate of 100 mmHg to 150 mmHg) This concentrated liquid is hereinafter referred to as "concentrated sample".

2. Separation and Purification (Step 3)

(1) Wakogel C-300 suspended in hexane was filled into a glass column (100φ) for 30 centimeters or so (about 300 g was filled therein)

(2) The column was equilibrated by flowing 1 column volume of hexane (3) About 500 g of the concentrated sample was applied on the column (4) As eluting solvents, in which a wax component is separated from the concentrated sample retained in the column, the following three types were used:

a. hexane:ether=100:0 (hereinafter referred to as "eluting solvent a")

b. hexane:ether=95:5 (hereinafter referred to as "eluting solvent b")

c. hexane:ether=90:10 (hereinafter referred to as "eluting solvent c")

(5) The separated wax component was subjected to acid hydrolysis, to perform a second purification (Step 4).

Results

The result of extraction of a wax ester carried out through the above method will be shown.

(1) About 3 L of wax component was extracted from 10 kg of *euglena*.

Based on the final collection rate, it is seemed that almost all the wax component can be collected through one time extraction with hexane.

(2) In performing filtration, since filterability was not good, sellite was spread over a filter paper to perform filtration.

(3) In performing concentration, when concentration is performed around 30° C., the concentrated liquid is cooled by the heat of volatilization, the viscosity of the wax component is increased from the surface, and bumping and blowout into the evaporator occur. In order to avoid this, concentration was performed around 50° C., so that the viscosity of the wax component was lowered and blowout into the evaporator by bumping could be avoided.

(4) About 500 g of the concentrated sample was applied on the column after equilibration is performed onto the column by introducing 1 column volume of hexane. 280 g or so was not retained and was directly eluted. Therefore, 2 column volume of eluting solvent was introduced to elute the component which is not retained, and the eluate was concentrated.

(5) Next, 3 column volume of eluting solvent b was introduced to elute and the eluate was concentrated. It was found that the wax component was eluted together with a yellow pigment.

(6) Next, in order to completely elute the wax component, 3 column volume of eluting solvent c was introduced to elute and condensation was performed.

At this time, about 240 g (300 mL) of the wax component could be collected.

Although a chlorophyll component could be separated, some pigments remained with a quite low concentration.

Discussion

Based on the above result, the column volume necessary for retaining 240 g or so of the wax component was about 2 L (about 1 kg), and the amount of the solvent required for elution was 9 column volume (about 18 L).

It can be seen that, when the wax component is 2.5 kg, the necessary column volume is about 24 L (about 12 kg), and the volume of the solvent required for elution is about 200 L or so.

As described above, hydrolysis is carried out after separation, so that the carbon chain of the wax ester is shortened, volatility is increased, and value as a fuel is enhanced.

Moreover, this wax ester can be effectively used as a bio-fuel.

*Euglena* is, as also used in health food and the like, an easily obtainable microorganism, which enables culturing in a large scale.

Quality wax ester can be collected by means of *euglena*, which is a microorganism as described above, so that clean energy is stably produced.

In the present example, the extraction with an organic solvent was carried out, but the extraction method is not limited thereto. For example, separation with water, a method using a carbon dioxide fluid, and physical methods such as compression can also be used.

The invention claimed is:

1. A method for producing an *euglena* highly containing a wax ester comprising;

a first step of aerobically culturing a microalga *euglena* under autotrophic conditions;

a second step of culturing the *euglena* in medium under nitrogen-starvation conditions and under autotrophic conditions to accumulate carbohydrate; and a third step of retaining the *euglena* under anaerobic conditions, to transform into a wax ester only carbohydrate stored in the *euglena*.

2. The method for producing an *euglena* highly containing a wax ester according to claim 1, wherein the nitrogen-starvation conditions are created by replacing the medium with a nitrogen source-deficient medium.

3. The method for producing an *euglena* highly containing a wax ester according to claim 1, wherein, in the first step, the aerobic culturing of the microalga *euglena* is started in a nitrogen source-free medium, the culturing is continuously and aerobically carried out with adjustment of the feeding amount and addition of a nitrogen source, and the feeding of the nitrogen source is stopped at the point where the cell concentration reaches a desired level, and in the second step, the *euglena* is further cultured under nitrogen-starvation conditions.

4. The method for producing an *euglena* highly containing a wax ester according to claim 1, wherein, in the first step, carbon dioxide gas is flowed into the medium, so that a carbon dioxide source and an oxygen source mixed thereto are provided.

5. The method for producing an *euglena* highly containing a wax ester according to claim 4, wherein the carbon dioxide gas is that emitted from power plants.

6. The method for producing an *euglena* highly containing a wax ester according to claim 1, wherein, in the third step, the anaerobic conditions are obtained by at least one method selected from inert gas ventilation, standing treatment, and concentration by centrifugation.

7. A method for producing a wax ester, comprising, a step of extracting an oily fraction with an organic solvent to obtain an extract using an *euglena* highly containing a wax ester, and concentrating the extract to obtain a wax component, wherein the *euglena* highly containing a wax ester is produced by a method for producing a *euglena* highly containing a wax ester that comprises a first step of aerobically culturing a microalga *euglena* under autotrophic conditions, a second step of culturing the *euglena* in medium under nitrogen-starvation conditions and under autotrophic conditions to accumulate carbohydrate, and a third step of retaining the *euglena* under anaerobic conditions, to transform into a wax ester only carbohydrate stored in the *euglena*, and a step of separating a wax ester from the wax component with a column to perform a first purification.

8. The method for producing a wax ester according to claim 7, wherein the concentrating is carried out within a temperature range of 50° C.±10° C.

9. The method for producing a wax ester according to claim 7, further comprising a second purification step of hydrolyzing the wax ester obtained by the step of performing the first purification.

10. The method for producing a wax ester according to claim 7, wherein, in the step of performing the first purification, hexane or a mixed solvent of hexane and ether to which ether is mixed in an amount of 10% by volume or less is used as an eluting solvent applied to the column.

11. The method for producing an *euglena* highly containing a wax ester according to claim 3, wherein, in the first step, carbon dioxide gas is flowed into the medium, so that a carbon dioxide source and an oxygen source mixed thereto are provided.

12. The method for producing a wax ester according to claim 7, wherein the nitrogen-starvation conditions are created by replacing the medium with a nitrogen-deficient medium.

13. The method for producing a wax ester according to claim 7, wherein, in the first step, the aerobic culturing of the microalga *euglena* is started in a nitrogen source-free medium, the culturing is continuously and aerobically carried out with adjustment of the feeding amount and addition of a nitrogen source, and the feeding of the nitrogen source is stopped at the point where the cell concentration reaches a desired level, and in the second step, the *euglena* is further cultured under nitrogen-starvation conditions.

* * * * *